(12) United States Patent
Langdon et al.

(10) Patent No.: US 12,121,431 B2
(45) Date of Patent: Oct. 22, 2024

(54) DURABLE UNDERWEAR ADAPTED FOR USE WITH ABSORBENT COMPONENT

(71) Applicant: The Procter & Gamble Company, Cincinnati, OH (US)

(72) Inventors: Frederick Michael Langdon, Cincinnati, OH (US); Bret Darren Seitz, West Chester, OH (US); Janice Faye Swinford, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 933 days.

(21) Appl. No.: 17/061,599

(22) Filed: Oct. 2, 2020

(65) Prior Publication Data

US 2021/0100698 A1 Apr. 8, 2021

Related U.S. Application Data

(60) Provisional application No. 62/911,435, filed on Oct. 7, 2019.

(51) Int. Cl.
*A61F 13/56* (2006.01)
*A41B 9/04* (2006.01)
(Continued)

(52) U.S. Cl.
CPC .............. *A61F 13/565* (2013.01); *A41B 9/04* (2013.01); *A61F 13/49006* (2013.01);
(Continued)

(58) Field of Classification Search
CPC .... A41B 9/12; A61F 13/565; A61F 13/49006; A61F 13/496; A61F 13/505;
(Continued)

(56) References Cited

U.S. PATENT DOCUMENTS 2,705,957 A * 4/1955 Mauro ................... A61F 13/70
604/397
3,909,851 A 10/1975 Garrou et al.
(Continued)

FOREIGN PATENT DOCUMENTS

CA 2255465 A1 6/2000
CA 2827795 A1 11/2013
(Continued)

OTHER PUBLICATIONS

International Search Report and Written Opinion; Application Ser. No. PCT/US2020/054532; dated Feb. 15, 2021, 16 pages.
(Continued)

*Primary Examiner* — Susan S Su
(74) *Attorney, Agent, or Firm* — William E. Gallagher

(57) ABSTRACT

A durable underwear brief panty adapted to accommodate an absorbent component is disclosed. The panty may include a crotch portion that exhibits a crotch longitudinal Elongation of 5 percent to 100 percent and a crotch longitudinal Tensile Modulus of 20 gf/mm to 100 gf/mm; and a crotch lateral Elongation of 50 percent to 200 percent and a crotch lateral Tensile Modulus of 2 gf/mm to 20 gf/mm. A combination of a brief panty and an absorbent pad, and an array including a brief panty product and an absorbent pad product, are also disclosed. The products are useful for management of incontinence.

19 Claims, 4 Drawing Sheets

(51) Int. Cl.
    *A61F 13/49*     (2006.01)
    *A61F 13/496*    (2006.01)
    *A61F 13/505*    (2006.01)
    *A61F 13/513*    (2006.01)
    *A61F 13/514*    (2006.01)
    *A41B 9/12*      (2006.01)
    *A61F 13/15*     (2006.01)

(52) U.S. Cl.
    CPC .......... *A61F 13/496* (2013.01); *A61F 13/505* (2013.01); *A61F 13/513* (2013.01); *A61F 13/51456* (2013.01); *A41B 9/12* (2013.01); *A61F 2013/15292* (2013.01); *A61F 2013/5147* (2013.01)

(58) Field of Classification Search
    CPC .............. A61F 13/513; A61F 13/51456; A61F 2013/15292; A61F 2013/5147; A61F 13/68; A61F 13/4906; A61B 9/04
    See application file for complete search history.

(56) References Cited

U.S. PATENT DOCUMENTS

| | | | |
|---|---|---|---|
| 4,355,425 A | 10/1982 | Jones et al. | |
| 5,085,653 A | 2/1992 | Levy | |
| 5,248,309 A | 9/1993 | Serbiak | |
| 5,562,648 A | 10/1996 | Peterson | |
| 6,258,455 B1 | 7/2001 | Clarke | |
| 6,287,286 B1 | 9/2001 | Akin et al. | |
| 6,393,621 B1* | 5/2002 | Redwine | A61F 13/49017 2/400 |
| 6,884,494 B1 | 4/2005 | Curro | |
| 7,118,639 B2 | 10/2006 | DeLucia et al. | |
| 7,322,966 B1 | 1/2008 | Deerin | |
| 7,458,961 B2 | 12/2008 | Carstens | |
| 7,462,173 B2 | 12/2008 | Carstens | |
| 7,846,145 B2 | 12/2010 | Carstens | |
| 8,099,794 B2 | 1/2012 | Carstens | |
| 8,117,675 B2 | 2/2012 | Strange et al. | |
| 8,262,638 B2 | 9/2012 | Carstens | |
| 8,348,918 B2 | 1/2013 | Carstens | |
| 8,454,570 B2 | 6/2013 | Carstens | |
| 8,679,085 B2 | 3/2014 | Ronstroem | |
| 9,980,861 B2 | 5/2018 | Deerin | |
| 10,441,480 B2 | 10/2019 | Griffiths | |
| 10,966,873 B2 | 4/2021 | Schneider | |
| 11,154,431 B1* | 10/2021 | Yip | A41B 17/00 |
| 11,395,774 B2* | 7/2022 | Skinner | A61F 13/539 |
| 2002/0004349 A1 | 1/2002 | Tsujiyama et al. | |
| 2002/0016580 A1* | 2/2002 | Wada | A41B 9/12 604/385.24 |
| 2003/0097109 A1 | 5/2003 | Bruce | |
| 2005/0120466 A1 | 6/2005 | Coenen et al. | |
| 2005/0142331 A1* | 6/2005 | Anderson | B32B 3/06 428/196 |
| 2005/0229293 A1* | 10/2005 | Miller | A41D 1/089 2/403 |
| 2006/0070163 A1 | 4/2006 | Beck | |
| 2006/0264869 A1 | 11/2006 | Carstens | |
| 2006/0264883 A1 | 11/2006 | Carstens | |
| 2006/0264884 A1 | 11/2006 | Carstens | |
| 2007/0012519 A1 | 1/2007 | Angielski | |
| 2007/0106354 A1 | 5/2007 | Carstens | |
| 2007/0245449 A1 | 10/2007 | Ehmsen et al. | |
| 2010/0249736 A1 | 9/2010 | Png et al. | |
| 2011/0172621 A1* | 7/2011 | Lee | A61F 13/51 604/385.03 |
| 2013/0226120 A1 | 8/2013 | Van De Maele | |
| 2014/0018763 A1 | 1/2014 | Evenson et al. | |
| 2014/0039432 A1* | 2/2014 | Dunbar | A61F 13/15577 604/394 |
| 2014/0257228 A1 | 9/2014 | Wang et al. | |
| 2014/0257229 A1 | 9/2014 | Wang et al. | |
| 2016/0089276 A1* | 3/2016 | Griffiths | A61F 13/532 604/378 |
| 2016/0100997 A1 | 4/2016 | Seitz | |
| 2016/0166447 A1 | 6/2016 | Toro | |
| 2016/0184146 A1* | 6/2016 | Tulk | A01N 37/06 604/385.15 |
| 2020/0000155 A1* | 1/2020 | Etienne | A61F 13/505 |
| 2021/0030605 A1* | 2/2021 | Kajanthan | A61F 13/4755 |
| 2021/0290447 A1 | 9/2021 | Sepello et al. | |
| 2022/0354710 A1 | 11/2022 | Sepello et al. | |
| 2023/0157375 A1 | 5/2023 | Seitz | |
| 2024/0000622 A1 | 1/2024 | Stanley et al. | |
| 2024/0050288 A1 | 2/2024 | Basius | |
| 2024/0065901 A1 | 2/2024 | Stanley | |

FOREIGN PATENT DOCUMENTS

| | | |
|---|---|---|
| CN | 101926709 A | 12/2010 |
| EP | 0811362 A1 | 12/1997 |
| EP | 1166738 A2 | 1/2002 |
| EP | 1370161 B1 | 12/2003 |
| EP | 2412353 A2 | 2/2012 |
| JP | 4266604 B2 | 2/2009 |
| KR | 100694187 B1 | 3/2007 |
| WO | 2004004619 A1 | 1/2004 |
| WO | 2013148749 A1 | 10/2013 |
| WO | 2013186577 A1 | 12/2013 |
| WO | 2015156686 A2 | 10/2015 |
| WO | 2021155397 A1 | 8/2021 |
| WO | 2022235734 A1 | 11/2022 |

OTHER PUBLICATIONS

All Office Actions; U.S. Appl. No. 18/645,742, filed Apr. 25, 2024.

Anonymous, "Femtis—Perioden Panties—Periodenslip Ella", XP093016146, Retrieved from the Internet: URL: https://web.archive.org/web/20210726170425/https://www.femtis.de/periodenslips/perioden-slip-ella-rot.html [retrieved on Jan. 20, 2023], Jul. 26, 2021, 9 pages.

Anonymous, "Inkontinenzslip: hydas.de", XP093016138, Retrieved from the Internet: URL: https://web.archive.org/web/20210412055014/https://www.hydas.de/inkontinenzslip [retrieved on Jan. 1, 2023], Apr. 12, 2021, 57 pages.

Anonymous, "Periodenpantys 2er-Pack Spitze schwarz—Secret Care", XP093016049, Retrieved from the Internet: URL: https://web.archive.org/web/20210415173928/https://www.schiesser.com/damenbekleidung-unterwaesche-slips-pants-periodenpantys-2er-pack-spitze-schwarz-secret-care.html [retrieved on Jan. 1, 2023], Apr. 15, 2021, 19 pages.

U.S. Appl. No. 18/645,742, filed Apr. 25, 2024, to Jill Marlene Orr et al.

* cited by examiner

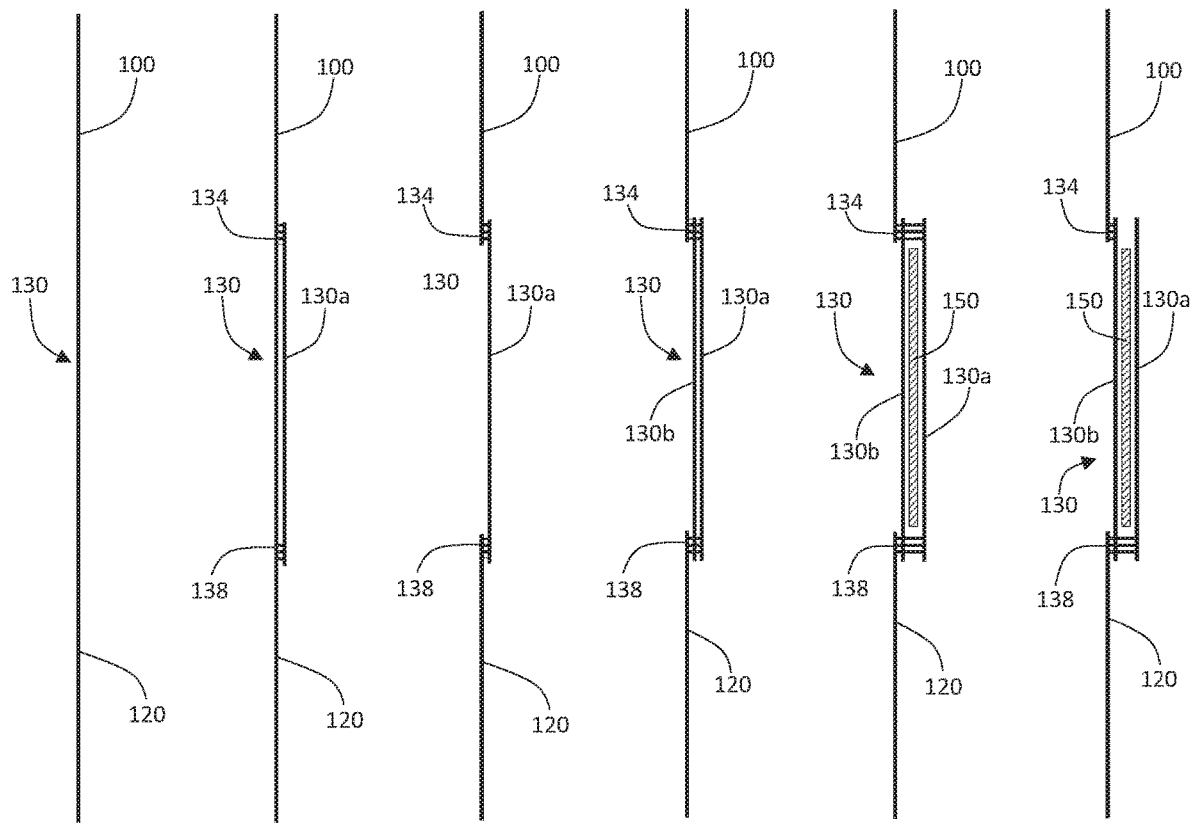

DURABLE UNDERWEAR ADAPTED FOR USE WITH ABSORBENT COMPONENT

BACKGROUND

In recent years population demographics in many developed countries have shifted toward middle-aged and older groups. These groups represent consumer markets with relatively increased demands for products addressed to concerns associated with aging.

One such concern is adult urinary incontinence. Urinary incontinence can result from or be exacerbated by a variety of health conditions, and for women, even normal experiences including childbearing or simply aging.

Disposable absorbent pants for adults suffering from urinary incontinence have been marketed for a number of years. These products have traditionally exhibited varying degrees of similarities in appearance, feel and bulkiness to disposable diapers or disposable children's training pants. Finding these similarities undesirable, many people experiencing only mild to moderate incontinence have preferred not to use these products, opting to use durable/washable absorbent underwear, or durable ordinary underwear in combination with a disposable absorbent incontinence pad held in place by/within the underwear.

A challenge presented in designing an absorbent system to be used to contain and absorb unintended small discharges of urine by a woman lies in the tendency of the urine, exiting the female urethra at relatively lower volume and velocity, to adhere and flow along skin surfaces and body contours (herein, "adhering flow"). Depending upon the woman's body position during an unintended discharge, adhering urine flow along external skin surfaces can find its way through gaps between the skin and containment features of the selected containment/absorbent system (e.g. underwear leg bands, cuffs and other containment features of absorbent underwear and/or pad), and thereby, escape capture by the absorbent portions of the system and soil surrounding portions of underwear, outer clothing, bedclothes, etc.

Currently available durable underwear panties do not sufficiently maintain contact between absorbent components and the wearer's body to reliably intercept adhering urine flow. On the other hand, if an absorbent pad is held too tightly against the wearer's body, its ability to expand with absorbed urine may be constrained, resulting in non-absorption and leakage.

Currently available durable absorbent underwear, and combinations of durable underwear and absorbent incontinence pads, have left room for improvement of containment performance. There is an unsatisfied need for an underwear/absorbent system that provides and maintains effective contact between an absorbent component and the wearer's body upon initial fit and during lower volume urine discharge, but can also rapidly accommodate swelling of absorbent components in the event of a larger volume discharge.

BRIEF DESCRIPTION OF THE DRAWINGS

FIGS. 3A-3F are schematic longitudinal cross sections of various alternative configurations of a brief panty as depicted in FIG. 2, taken along line 3-3 in FIG. 2.

DEFINITIONS

Figure 1:
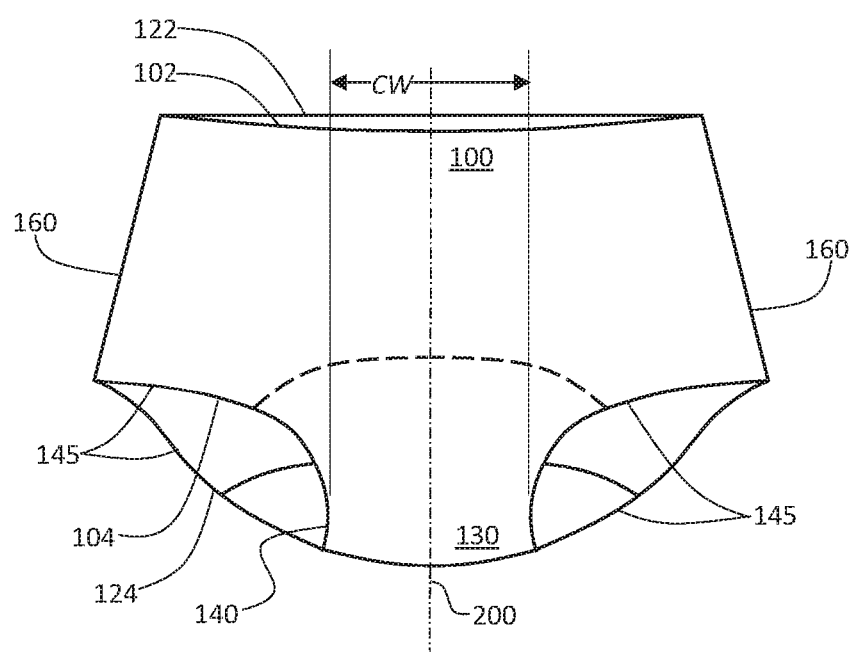
FIG. 1 is a simplified depiction of an example of a brief panty, as it would appear laid out flat on a horizontal planar surface, front waist portion facing up.

"Array of products" means first and second structurally differing products concurrently offered for sale and being associated with a common trademark, each product bearing, or being associated with packaging that includes, information that informs a purchaser of either product that the first product is designed for use in combination with the second product, or vice versa.

With respect to a panty in an opened configuration, laid out flat on a horizontal planar surface, "longitudinal" refers to a direction generally perpendicular to a line tangent each of the left and right leg opening edges where they are closest the front waist edge. With respect to a panty in an assembled configuration, laid out flat on a horizontal planar surface, front waist portion facing up, "longitudinal" refers to a direction generally perpendicular to a line tangent each of the left and right leg opening edges where they are closest the front waist edge. "Length" refers to a dimension measured along the longitudinal direction.

With respect to a panty in an opened configuration, laid out flat on a horizontal planar surface, "lateral" refers to a direction generally parallel to a line tangent each of the left and right leg opening edges where they are closest the front waist edge. With respect to a panty in an assembled configuration, laid out flat on a horizontal planar surface, front waist portion facing up, "lateral" refers to a direction generally parallel to a line tangent each of the left and right leg opening edges where they are closest the front waist edge. "Width" refers to a dimension measured along the lateral direction.

With respect to a wearable garment such as a panty, "durable" means made predominately (as a percentage or fraction of its outward-facing surface area) of cloth material that is knitted and/or woven from natural, semi-synthetic or synthetic fiber, thread or yarn, and which may be normally laundered or hand-washed and dried for reuse/re-wear a plurality of times without substantial destruction thereto.

A yarn, thread, fiber or filament material, or a composite thereof, is considered to be "elastic" or "elastomeric" for purposes herein if, when axial tension is applied to the material or composite, the material may be extended to an elongated length of at least 150% of its original relaxed length (i.e. can extend at least 50%), without rupture or breakage which substantially damages the material or composite, and when the force is removed from the material or composite, the material or composite recovers at least 40% of such elongation. "Elongation," used herein to quantify and express an amount of strain imparted to an elastic strand in the direction of its axis, means: [(strained length of the strand–length of the strand before straining)/(length of the strand before straining)], ×100%.

With respect to two opposing surfaces of a layer component of a panty, "wearer-facing" refers to the surface that faces the wearer's skin when the panty is worn normally; and "outward-facing" refers to the surface that faces away from the wearer's skin. With respect to two distinct layered components of a panty, the "wearer-facing" component is the component that is disposed closer to the wearer's skin when the panty is worn normally; and the "outward-facing" component is the component that is disposed farther from the wearer's skin.

Figure 4A:
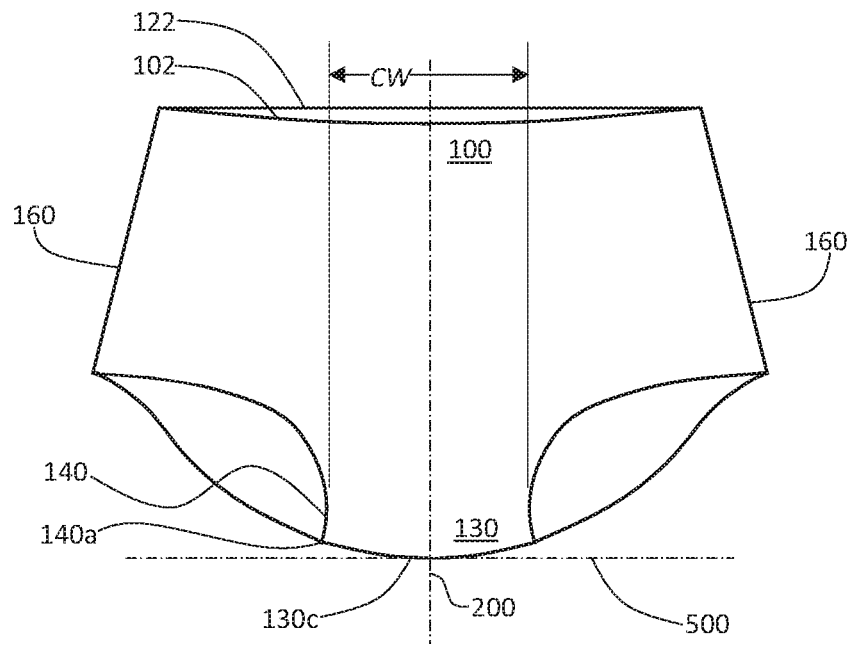
FIG. 4A is a simplified depiction of an example of a brief panty, as it would appear laid out flat on a horizontal planar surface, front waist portion facing up.
Figure 4B:
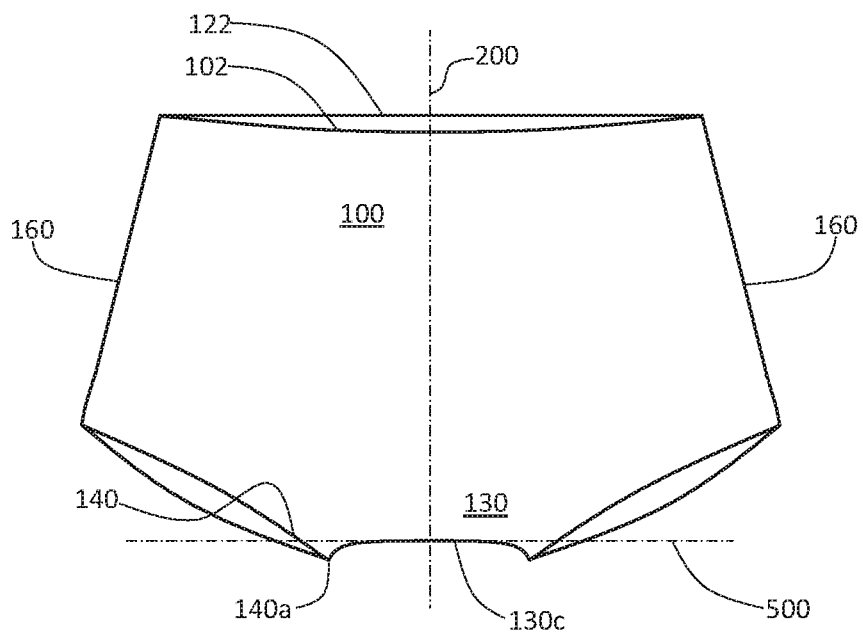
FIG. 4B is a simplified depiction of an example of a shorts panty, as it would appear laid out flat on a horizontal planar surface, front waist portion facing up.

For purposes herein, a "brief panty" is distinguished from a "shorts panty" in an underwear garment by the configuration of the leg edges with respect to the crotch portion, resulting from the manner in which the component materials are shaped, sized, proportioned and seamed or otherwise affixed together. FIG. 4A depicts an example of a brief panty and FIG. 4B depicts an example of a shorts panty. When the garment in its assembled condition is laid out flat on a horizontal planar surface, front waist portion facing up, and a lateral crotch tangent line 500 is drawn perpendicularly to longitudinal axis 200 and tangent to the point at which the crotch portion lower profile 130c intersects the longitudinal axis 200, for a brief panty, the lowermost points 140a along the crotch leg opening edges 140 are disposed along or above the crotch tangent line 500 (i.e., toward the front waist edge 102) (see FIG. 4A); and For a shorts panty, the lowermost points 140a along the crotch leg opening edges 140 are disposed below the crotch tangent line 500 (i.e., away from the front waist edge 102) (see FIG. 4B).

DESCRIPTION OF EMBODIMENTS

As noted in the Background, a problem presented in designing an absorbent system to be used to contain and absorb unintended (incontinent) small discharges of urine by a woman results from adhering urine flow. As a result of female anatomical features, typical surface chemistry of human skin (which can result in hydrophilicity of the skin surface) and the composition of urine, adhering flow has always been a feature of low to moderate female adult incontinence. If features of a chosen containment/absorbency system do not reliably hold absorbent materials against the wearer's skin to intercept adhering flow, leakage can result.

Many women prefer brief panties rather than shorts panties for ordinary daily wear. This is due to issues of comfort; unlike a shorts panty, a brief panty ordinarily will not ride up and bunch about the legs from changes of body position, and thereby be a source of unwanted concentration of material bulk, tightness about the legs or other discomfort under outer clothing. To the best of the inventors' knowledge and belief, however, a durable adult incontinence brief panty that reliably protects against leakage of adhering flow through a variety of body movements and positions and over a reasonable duration of wear/use has not been marketed to date. This includes brief panties with built-in, durable absorbent structures, and brief panties with which separate absorbent pads have been used. Currently marketed panty products do not effectively hold absorbent structures against the body through various body movements, over a reasonable duration of wear/use.

Further, many types of separate incontinence pads intended to be worn against the body inside underwear (for example, ALWAYS DISCREET incontinence pads, manufactured and sold by The Procter & Gamble Company, Cincinnati, OH) have absorbent core structures that include particles of absorbent material known as absorbent gelling material (AGM) or superabsorbent polymer (SAP) (hereinafter, "AGM"), which is well-known in the fields of designing and manufacturing diapers, training pants and adult incontinence products. In such products the AGM particles are typically distributed across and throughout an absorbent core structure or absorbent layer within the pad. In some examples the AGM particles may be dispersed throughout a matrix of a batt of fibers (such as cellulose fibers), and may be held in place within the matrix via consolidation of the fibers, by a binder or adhesive, or a combination thereof. In some examples a distributed pattern of small individualized deposits of AGM particles may be held in place in small enveloping compartments formed between two layers of nonwoven web. In other examples a distributed pattern of small individual deposits of AGM particles may be held in place on a substrate web material by an adhesive. In any case, however, individual AGM particles can typically absorb multiples of their weight in urine. As they absorb urine, the particles form gel masses in which the urine is effectively captured and held, and the gel masses swell as urine is absorbed. The aggregated swelling of the gel masses can substantially increase the overall bulk of the absorbent core structure.

Other types of absorbent materials, even absorbent materials such as cellulosic fiber (including wood pulp and cotton fiber), can also swell as they take on fluid (although to a more limited extent than AGM particles). Nevertheless, as individual fibers and/or groups of fibers swell with absorbed fluid, their swelling can aggregate to cause the bulk of the absorbent structure as a whole to increase.

Such increased bulk, together with the weight of the absorbed urine, can complicate the containment challenge, by further straining panty components and making them less effective at holding the pad against the wearer's body. It is not a satisfactory solution to simply make the panty fit more tightly (by, e.g., smaller material dimensioning for a given wearer size and/or selecting materials with greater tensile modulus), because a tighter fit can compress or constrain expansion of the absorbent components, and thereby restrict their absorption capability, and can also make the panty uncomfortable.

It has been learned, however, that a brief panty may be designed that more reliably and comfortably holds an absorbent pad assembly against a wearer's body, in a better position to intercept adhering urine flow, capture the urine in the absorbent material before it can escape, and permit expansion of the absorbent components, initially and over a reasonable duration of wear/use of the pad.

Figure 2:
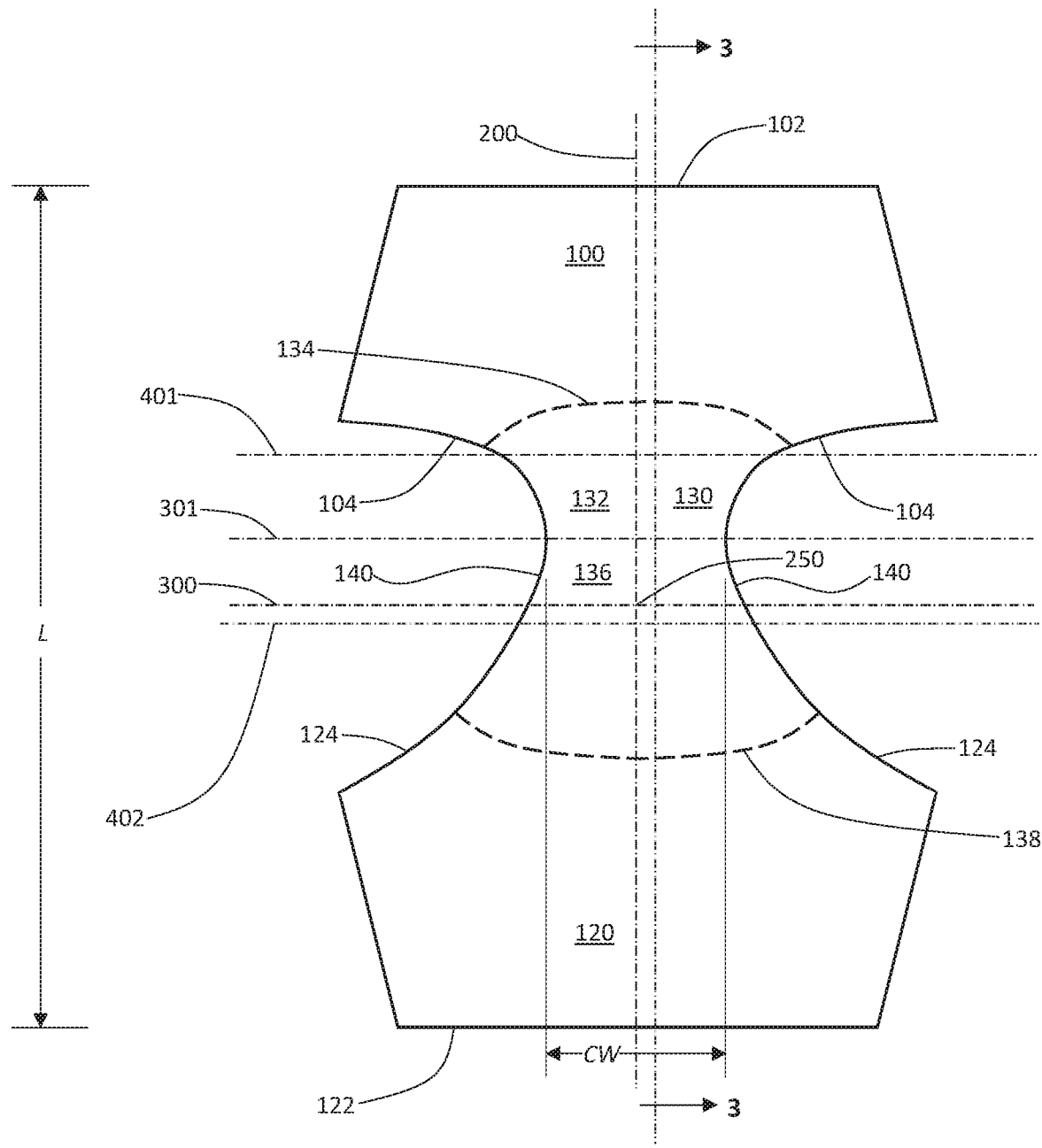
FIG. 2 is a depiction of the brief panty of FIG. 1, in an opened configuration wherein the front and rear waist portions have been separated at the hip portions or hip side seams, as it would appear laid out flat on a horizontal planar surface, wearer-facing surfaces facing up.

Referring to FIGS. 1 and 2, a brief panty may include a front waist portion 100, a rear waist portion 120 and a crotch portion 130 bridging the front and rear waist portions. Front waist portion 100 has a front waist edge 102, and left and right front leg opening edges 104. Rear waist portion 120 has a rear waist edge 122, and left and right rear leg opening edges 124. Crotch portion 130 has left and right crotch leg opening edges 140. Referring to FIG. 2, for purposes herein, crotch portion 130 is the portion of the panty, at a minimum, lying between crotch portion minimum front extent 401 and crotch portion minimum rear extent 402, longitudinally centered about crotch portion lateral axis 301 (which is drawn along the smallest width dimension CW measured between the crotch leg opening edges 140), plus 10 percent of the overall length L of the panty to the front and the rear of the crotch portion lateral axis 301. As suggested by FIG. 2, it may be desired that the crotch portion lateral axis 301 be disposed forward of the lateral axis 300 (which equally divides overall length L), rather than be co-located with lateral axis 300, for purposes of better fit about an adult female wearer's legs and lower torso. Thus, the respective boundaries between crotch portion 130 and front and rear waist portions 100, 120 for purposes herein are independent of the location(s) of any seams such as seams 134, 138 that may be present to join material(s) included in the crotch portion and material(s) included in the front and rear waist portions 100, 120.

Material(s) forming one or both of forward and rearward portions 132, 136 of crotch portion 130 may be continuous with material(s) forming front and rear waist portions 100, 120, or alternatively, one or both of forward and rearward portions 132, 136 of crotch portion 130 may be substantially formed of one or more sections or layers of material that are distinct from material(s) substantially forming one or both of front and rear waist portions 100, 120, and may be joined to front and rear waist portions 100, 120 at one or both of forward seam 134 and rearward seam 138.

In one example, referring to FIG. 3A, front waist portion 100, crotch portion 130 and rear waist portion 120 may be formed partially or entirely of a single, continuous section of material. In another example, referring to FIG. 3B, front waist portion 100, crotch portion 130 and rear waist portion 120 may share a single, continuous section of material, and a second layer of material 130a may be added to crotch portion 130 on the wearer-facing side as shown, or on the outward-facing side, wherein the second layer as affixed to the first section of material via, e.g., stitching/sewing, adhesive bonding, thermal bonding (fusing or welding) or other suitable attachment/joining mechanism (hereinafter, attachment mechanism) at forward and rearward seams 134, 138. In another example, referring to FIG. 3C, the sections of materials respectively forming front waist portion 100, rear waist portion 120 and crotch portion 130 may be separate and distinct, and joined via an attachment mechanism at forward and rearward seams 134, 138. In another example, referring to FIG. 3D, the sections of materials respectively forming front waist portion 100, rear waist portion 120 and crotch portion 130 may be separate and distinct, and joined via an attachment mechanism at forward and rearward seams 134, 138; and crotch portion 130 may include at least inner and outer layers of material 130a, 130b. One of the configurations depicted in FIGS. 3B-3D may be preferred because these configurations may provide the designer with greater flexibility in selection of the respective materials for the waist and crotch portions with respect to appearance, feel, weight, breathability, elongation, stretch characteristics and cost. Generally, the configurations depicted in FIGS. 3A-3D would be applicable for a brief panty that is not in and of itself substantially absorbent, but rather, is configured to work with a discrete, separate absorbent incontinence pad worn inside and held in place against the body by the panty. The elongation and stretch characteristics described below would be applicable to the one, or more layers of material in combination, present in crotch portion 130.

FIG. 3E depicts an example of a brief panty configured to be absorbent and used for incontinence management by itself, or else to provide some desired absorption capacity to supplement or be supplemented by that of a separate pad to be worn inside the panty. The crotch portion 130 may include inner and outer layers 130a, 130b, forming a closed envelope structure about an absorbent pad 150. Inner and outer layers 130a, 130b may be joined to each other via a suitable attachment mechanism about the perimeter of the absorbent pad 150 to retain it in place within the envelope structure.

Absorbent pad 150 may be formed of or include any suitable absorbent fibrous or absorbent foam material having a durable composition and structure that can withstand laundering or hand washing and drying, without substantial destruction or degradation, over a plurality of uses/wearings and washings. In some examples absorbent pad 150 may include or consist of a single layer or combination of layers of woven or knitted cotton, other natural plant-based fibrous material, rayon, polyester, polyamide (e.g., nylon) or a combination thereof. Fibers of the constituent material are preferably hydrophilic so as to impart absorbency to a pad from which they are formed. In some examples the pad 150 may be formed of knitted material that will stretch in at least a lateral and in some examples both lateral and longitudinal directions.

In some examples it may be desired that absorbent pad 150 float within the envelope structure, meaning that it is not affixed to any portion of the enveloping structure including layers 130a, 130b. This will permit the layers 130a and/or 130b to stretch to accommodate swelling of the absorbent pad, unconstrained by the structure of the pad 150. In some examples it may be desired that absorbent pad 150 partially float within the envelope structure, wherein the pad is affixed to the surrounding structure along locations that do not include longitudinal side edges, forward or rearward ends, or both. In some examples this may mean that middle portions of the absorbent pad (i.e., along or proximate either the longitudinal 200 or lateral 300 axis) are affixed to one or both layers, or only a forward portion or edge, or only a rearward portion or edge. Generally, however, it may be deemed undesirable for absorbent pad 150 to be affixed to the envelope structure or one of layers 130a, 130b at oppositely-disposed locations along longitudinal side edges of the absorbent pad. For example, if a single line or path of stitching lying substantially or approximately along the longitudinal axis of the pad affixes it to one or both of layers 130a, 130b, pad 150 will be held in a laterally centered position within the envelope, but lateral stretch of layers 130a, 130b will not be constrained by the structure of the pad.

In examples within contemplation of FIG. 3E and the description above, inner layer 130a should be a liquid permeable durable fabric material, which will allow urine to readily pass therethrough to the absorbent pad 150. Accordingly, the material should have a suitable combination of porosity and hydrophilicity. It may be preferable that the material not be formed predominately of a highly hydrophilic, highly absorbent material such as processed cotton or rayon, because while such materials readily accept aqueous fluid, they also tend to absorb and retain it and do not readily release it; and thus an inner layer 130a formed of such a material such can have a sustained wet and uncomfortable feel for the wearer following an incontinent discharge of urine. Thus, it may be preferred that inner layer 130a be formed predominately of a material possessing good wicking properties, such as a synthetic polymeric material, for example, polyester or a polyamide such as nylon. For example, suitable nylons may be preferred in some circumstances because they are ordinarily hydrophilic and easily cleaned, and not particularly absorbent, but can still impart good wicking properties to a fabric formed of them. Outer layer 130b may be formed of or include a sublayer of liquid-impermeable material suitable to prevent urine absorbed by pad 150 from passing out through the outer layer 130b. Outer layer 130b may be formed of or include a sublayer of liquid-impermeable film, which may be manufactured to be vapor permeable or "breathable". A variety of such films are known in the arts relevant to diapers, training pants, feminine hygiene pads and incontinence products.

FIG. 3F depicts an example of a brief panty configured to accommodate a removable absorbent insert pad 150. FIG.

3F may have a configuration, and be formed of and/or include materials, similar to the example depicted in FIG. 3E described above, with a difference in the envelope structure. As suggested in the figure, the envelope structure may be open along a location such as along a front location of crotch portion 130, so as to provide a pocket that permits insertion and removal of an absorbent pad 150. In this example, pad 150 may be durable and washable as described above, or alternatively, may be configured for single use and then disposal, being formed of and including materials similar to those typically included in a disposable feminine hygiene pad or incontinence pad. Thus, in this example, pad 150 may also include its own liquid impermeable backsheet.

For purposes that may include odor control, in some examples any, some or all of the materials present in the crotch region, including but not limited to inner layer 130a and absorbent layer 150 (if present) may be formed of component material(s) that include a metal, metal alloy or metallic compound having antimicrobial properties. Examples may include copper, silver, zinc and aluminum, and alloys and/or compounds thereof. The incorporation or "infusing" of such materials into threads or yarns that may knitted is known in the art. Other suitable odor control agents may be incorporated as well.

When the brief panty is fully assembled the front and rear waist portions 100, 120 are joined together at left and right side hip portions 160, resulting in the formation of waist opening edge 110 and left and right leg opening edges 145. (See FIG. 1.) In some examples, the front and rear waist portions 100, 120 may be formed of a single, continuous section of material without side seams ("seamless" construction). In other examples, the front and rear waist portions 100, 120 may be formed of distinct sections or separated portions of material and joined at hip side seams extending approximately vertically or longitudinally along the hip portions 160.

Any or all of front waist portion 100, rear waist portion 120 and crotch portion 130 may be formed of a knitted material, which may be a stretch knit material that includes elastic strands or threads that impart to, or enhance, elastic extensibility and contractibility of the material. A variety of suitable knitted and stretch knit materials having varying and selectable elongation and tensile modulus properties are known in the arts of garment manufacturing and are commercially available. Suitable stretch knit materials are currently available from Schoeller Textil AG, Sevelen, Switzerland. Suitable materials may be selected for their elongation and tensile modulus properties, and also for their weight, breathability, moisture wicking properties, tactile feel against the skin and cost. In some examples the material may be knitted from non-elastic and elastic fibers, threads or yarns, wherein the elastic components are formed of or include an elastomeric material such as elastane (for example, spandex or LYCRA, available from The Lycra Company, Wilmington, Delaware).

The brief panty may be further configured with a waist band structure (not specifically shown) at the waist edges, and leg band structures (not specifically shown) at the leg opening edges. Waist band and leg band structures may be formed of folded-over portions of the materials forming the front waist portion, rear waist portion and/or crotch portion. In some examples a plurality of strands or one or more strips of elastomeric material may be captured and contained within the folded-over portions, to supplement elasticity and contractile forces within the material itself, improve the ability of the panty to stay in place on the wearer's body during wear, and to contain urine. In some examples a separate and distinct waist band assembly and/or leg band assemblies may be provided and affixed via suitable attachment mechanism, to the front waist, rear waist and crotch portions proximate to, or in a position to define, the waist opening edge and leg opening edges. Elastic band assemblies suitable for forming separate waist bands and leg bands for underwear such as a brief panty are known in the arts of garment manufacturing and are commercially available. Elastic waist and leg band structures may be desired to better hold the panty in place on the wearer's body, and elastic leg band structures may be desired further to provide supplemental tensile force about the leg openings that helps hold an absorbent pad against the wearer's body in the crotch region of the body.

Several features have been identified as effective, when included in combination in a brief panty, for improving containment performance when the panty includes or is used with an absorbent pad.

It may be desired that the brief panty have sufficient width in the crotch portion, with the material thereof in the relaxed condition, to provide satisfactory lateral coverage over an absorbent pad. Accordingly, it may be desired that the crotch portion 130 have a relaxed width CW, measured from right leg edge to left leg edge at the narrowest part of the crotch portion, of at least 8.0 cm, more preferably at least 9.5 cm, and even more preferably at least 11.0 cm. This is believed to be wider than is typical for currently available underwear brief panties of any size.

It may be desired that the crotch portion exhibit a sufficient degree of longitudinal and lateral elongation to accommodate an increase in bulk of an absorbent pad resulting from absorption and swelling, and prevent swelling of the pad from creating gaps between, e.g., leg bands and the wearer's skin. At the same time, it may be desired that longitudinal elongation be more limited than lateral elongation, to help maintain a pad within the crotch portion in position against the wearer's body. Accordingly, it may be desired that the crotch portion exhibit lateral Elongation of 50 percent to 200 percent, and a longitudinal Elongation of 5 percent to 100 percent. In some examples, it may be desired that materials be selected to form the crotch portion such that they result in a ratio of lateral Elongation to longitudinal Elongation be 3:1 or greater.

In combination with longitudinal and lateral elongation capability, it may be desired that the crotch portion have Tensile Modulus properties that are selected to strike a balance between suitably allowing the crotch portion to expand in width and length to accommodate an increase in bulk of an absorbent pad as urine is absorbed, while still serving to effectively hold the pad in place against the wearer's skin so that it will continue to intercept adhering flow and absorb the urine. Accordingly, it may be desired that the crotch portion be formed of material(s) that impart to it a longitudinal Tensile Modulus of 20 gf/mm to 100 gf/mm, and a lateral Tensile Modulus of 2 gf/mm to 75 gf/mm, more preferably 2 gf/mm to 40 gf/mm, and even more preferably 2 gf/mm to 20 gf/mm. In some examples, it may be desired that materials be selected to form the crotch portion such that they result in a ratio of longitudinal Tensile Modulus to lateral Tensile Modulus of 3:1 or greater.

It will be appreciated from the description above that, generally, the stretch characteristics desired for the material(s) of the crotch portion, are, generally, relatively higher Elongation and relatively lower Tensile Modulus in the lateral direction, in combination with relatively lower Elongation and relatively higher Tensile Modulus in the longitudinal direction. It has been found that this anisotropic combination of direction-oriented stretch characteristics in the material(s) of the crotch portion serves to help satisfactorily address and resolve the inherent conflict between the goals of holding an absorbent pad snugly against the wearer's body in position to intercept adhering urine flow, while providing stretch that accommodates swelling and increased bulk of the pad as it absorbs urine.

In the ranges of values for Elongation and Tensile Modulus set forth above, it is contemplated that any combination of narrower ranges (sub-ranges) within the broader ranges set forth may be selected under particular circumstances, as may be desired according to, for example, panty size and style (e.g., bikini, hip hugger, control brief, etc.); absorbent pad size(s) expected to be used with the panty, elongation and modulus features of material(s) used to form waist portions, etc. By way of non-limiting example, selected sub-ranges for crotch lateral Elongation may be 50 percent to 100 percent, or 100 percent to 200 percent, or 75 percent to 150 percent, etc., all being within the broader range set forth above, and all such permutations of sub-ranges being within contemplation of the present disclosure.

For purposes herein, Elongation and Tensile Modulus are measured using the methods set forth below.

In combination with either or both the above features of Elongation and Tensile Modulus and in some examples in combination particularly with the above-described Elongation, it may also be desired that material(s) used to form the crotch portion not impart the crotch portion with an excessive Poisson Contraction Effect upon lateral stretching/extension. For purposes herein, the Poisson Contraction Effect quantifies and expresses the extent to which a material will contract along a first direction in a plane, when elongated/strained along a second direction in the plane perpendicular to the first direction. When the crotch portion is strained/elongated in a lateral direction to accommodate expansion of an absorbent pad, excessive Poisson Contraction Effect in the longitudinal direction can work against the purpose of allowing expansion of the crotch portion to accommodate an increase in bulk of the absorbent pad. Accordingly, it may be desired that the material(s) of the crotch portion be selected such that as assembled they will exhibit Poisson Contraction Effect, resulting from to lateral stretch/extension, no greater than 0.4, more preferably no greater than 0.2, and even more preferably no greater than 0.15. For purposes herein Poisson Contraction Effect measured according to the Poisson Contraction Effect method set forth below.

Many knitted fabrics exhibit anisotropic planar tensile elongation properties, having a maximum elongation capability along a first direction and a minimum elongation capability along a second direction substantially perpendicular to the first direction. Woven fabrics of some types also exhibit anisotropic planar tensile elongation properties, having a maximum elongation capability along a first direction and one or two lesser and/or minimum elongation capabilities along the two directions that are substantially 45 degrees from the first direction. For purposes of providing herein-described elongation capabilities to the crotch portion 130, it may be desired the material(s) selected to form one or all layers of the crotch portion be oriented within the crotch portion such that their directions of maximum elongation capability lie substantially along the lateral direction, relative the brief panty. It may be further desired that knitted fabric(s) be used to form one, more or all of the wearer-facing, outward-facing and any intermediate layers of the crotch portion because knitted fabric(s) of selected knit types may be identified that exhibit the desired limited Poisson Contract Effect as discussed above.

In some examples, the material selected to form or be included in crotch portion 130 may be a rib knit fabric. The ribs of the knit may be oriented so as to be substantially aligned with the longitudinal direction. In this orientation, the particular configuration of rib knit fabric permits it to elongate substantially in the lateral direction with relatively low accompanying longitudinal contraction. Thus, a rib knit fabric with ribs oriented substantially longitudinally may be desired for purposes of providing the benefits of limited Poisson Contraction Effect as discussed above.

Where the crotch portion is formed of or includes only a single layer of material as suggested in, by way of example, FIGS. 3A and 3C, the material forming the single layer may be selected so as to have the stretch characteristics described above. Where the crotch portion is formed of a plurality of layers as suggested in, by way of example, FIGS. 3B and 3D, the materials forming the plurality of layers may be selected so as to have, in combination, the stretch characteristics described above. Where the crotch portion is configured to contain an absorbent pad between layers as suggested, by way of example, in FIGS. 3E and 3F, material(s) forming the outer layer(s) 130b (to the outward-facing side of the absorbent pad 150) may be selected so as to have the stretch characteristics described above, in combination. Alternatively, all materials forming the inner 130a and outer 130b layers may be selected so as to have the stretch characteristics described above, in combination.

In combination with the features described above applicable to the materials of the crotch portion 130, materials forming or included by the waist portions 100, 120 may be selected so as to have particular stretch characteristics that cooperate with the materials of the crotch portion to have the desired expandable but snug pad holding properties of the materials of the crotch portion. Accordingly, it may be desired that one or both of the front waist portion 100 and rear waist portion 120 be formed of or include knit material(s) that in combination, for the waist portion: a maximum longitudinal elongation of 200% and a longitudinal tensile modulus of 5 gf/mm to 25 gf/mm, more preferably 10 gf/mm to 20 gf/mm, and even more preferably 13 gf/mm to 17 gf/mm; and a maximum lateral elongation of 200% and a lateral tensile modulus of 5 gf/mm to 25 gf/mm, more preferably 10 gf/mm to 20 gf/mm, and even more preferably 13 gf/mm to 17 gf/mm.

It is contemplated that a brief panty having any desired combination of the features described herein may be effectively used in combination with an absorbent incontinence liner or pad of any suitable configuration configured to be used/worn beneath a pair of underwear panties. Suitable examples typically include a wearer-facing, liquid permeable topsheet; an outward-facing, liquid impermeable backsheet, and an absorbent structure disposed between the topsheet and the backsheet. The typical liner or pad is sized and shaped so as to be held within and by underwear panties, reasonably comfortably, against the user/wearer's body in the crotch region. Many suitable liners or pads also include a deposit of adhesive on an outward-facing surface of the backsheet, provided to enable the user/wearer to adhere the pad to the wearer-facing surface of the panty in the crotch region, such that the pad will be more securely held in appropriate position within the panty during use/wear. The liner or pad may include features known in the art as "wings," provided to be wrapped about the insides of the panty leg opening edges, for further benefit in holding the pad in position within the panty during use/wear; such wings may also include deposits of adhesive on outward-facing surfaces (which, following wrapping about leg opening edges, face the wearer). Deposits of adhesive on the outward-facing surface of the backsheet may be continuous or intermittent, and may have any desired pattern including a pattern of longitudinal or lateral strips. Suitable non-limiting examples of liners and pads are currently marketed by The Procter & Gamble Company, Cincinnati, Ohio, under the brand names/trademarks ALWAYS DISCREET. Other suitable non-limiting examples are also described in, for example, EP 3 034 055 B1, incorporated herein by reference to the extent not inconsistent herewith. Absorbent core structures of many suitable examples will include absorbent materials or accumulations and/or combinations thereof that volumetrically expand or swell as they absorb liquid, for example, accumulations of particles of absorbent gelling material (also known as superabsorbent polymer), batts of cellulose fibers, collapsed, open-cell absorbent foams (such as collapsed open-cell foams formed from High Internal Phase Emulsions (HIPEs)), etc. It will be appreciated that a brief panty having features as described herein is particularly suited to accommodating such expansion or swelling as it aggregates to swell the liner or pad as a whole, while maintaining an improved level of contact between the liner or pad and the user/wearer's body.

It is contemplated that a brief panty product within contemplation of the description above may be offered for sale as one of two or more products in an array that includes an incontinence pad product. In some examples, the respective products of the array can be accompanied by information matching or coupling them not only by associated trademark, but also by, e.g., advertised size, advertised use (e.g., "moderate" or "light" incontinence needs, "daytime" or "nighttime" use, etc.), panty design (e.g., bikini, hip hugger, control brief, etc.), complementary or compatible lengths, crotch portion widths or other dimensions, or other features making them particularly adapted, complementary or compatible for use with one another.

In some examples, a pad and a panty in an array may include respectively compatible/co-functioning attachment components. In one particular example, a pad in an array may include one component of a hook-and-loop fastening system such as a hooks component, and a panty in the array may include the complementary/co-functioning component such as a loops component, the respective components being disposed at locations that facilitate suitable location and holding of the pad within the panty for use. In another example, the pad in array may include a deposit of adhesive on an outward-most facing surface, adapted to enable the user to affix the pad to an inward-most (wearer-facing) surface of the panty. In such example, it may be desired that the adhesive deposit be disposed at or be present at location(s) more proximate a longitudinal axis of the pad, rather than location(s) more proximate side edges of the pad. This is to reduce chances that the pad structure will restrict lateral stretch of the panty in the crotch portion. Thus, in a particular example, a pad may have a longitudinal strip of deposited adhesive along or more proximate the longitudinal axis of the pad, while not having adhesive deposits more proximate the side edges at opposing (i.e., left and right) locations.

Measurement Methods

General Sample Preparation

Each of the measurements below is to be conducted on 10 separate like samples (from 10 separate like samples of brief panties) and the average of the 10 separate like samples is considered to be the measurement for that specific sample set.

Samples are collected from the crotch portion (130) of the panty. Samples are cut from about the longitudinal and lateral center of the crotch portion. In testing for longitudinal properties, samples are cut in a rectangular shape, 6 cm long (dimension measured in the longitudinal direction) and by 2 cm wide (dimension measured in the lateral direction). In testing for lateral properties, samples are cut in a rectangular shape, 6 cm wide (dimension in the lateral direction) by 2 cm long (dimension measured in the longitudinal direction).

The sample should be cut with a sharp knife or suitably sharp cutting device designed to precisely cut the sample. Data collection is accomplished through a combination of manual measurements, machine elongation measurements and machine load measurements.

The testing is performed under ambient room conditions (temperatures from between 15° C. to 35° C. and relative humidity from between 35% to 75%). Samples are conditioned for at least two hours prior to testing under the same conditions.

All linear dimensions are measured manually by ruler within the ordinary x-y plane, using a ruler that is traceable to NIST or other standards organization.

Tensile Modulus

The Tensile Modulus of the sample is determined by stretching in the direction of the sample's longer dimension using a constant rate of extension tensile testing machine with computer interface, e.g., Instron; MTS; Zwick; etc., using a load cell for which the loads measured are within 10% to 90% of the limit of the cell, and ensures accuracy of a 5N load to 0.1N. The instrument is equipped with a single line contact grips, wider than 3 cm (ensures wider than the short axis of the sample). Prior to testing, calibrate the equipment according to the instruments manufacturer's recommendations.

The grips of the tensile testing machine consist of air actuated grips designed to hold the sample. No slippage should be permitted between the sample and the grips. The distance between the lines of gripping force (distance from one grip to the next, along the axis of the machine's elongation) should be 3 cm as measured by a steel rule held beside the grips. This distance will be referred to from here on as the "starting gauge-length".

The sample is mounted in the grips with its long axis parallel to the direction of applied elongation, and the center line of the long axis of the sample centered in each grip. 1 cm of each end of the sample's long axis is inserted into each grip, leaving 4 cm of the long axis of the sample between the grips. The starting gauge-length of 3 cm ensures some slack in the sample at the start of the test.

After the sample is mounted, the machine's load channel is set to zero (this eliminates the weight of the sample in the calculations). The grips are slowly moved apart at 5.08 cm/min (2.0 in/min) until a load of 5 gf (grams-force) is attained. The separation between the grips at this position is recorded as $L_0$.

($L_0$=starting gauge-length+additional machine extension to reach 5 gf).

After the 5 gf load is attained, extend the sample at a rate of 50.8 cm/min (20 in/min) with a data acquisition rate of 50 Hz. Extend until either a stress of 15 gf/mm is reached, or the sample breaks.

For stress calculation, the thickness of the material is neglected, hence the stress values are recorded in units of gf/mm. Stress is calculated by dividing the load in the sample, as recorded by the load cell, by the sample width (short axis as measured in units of mm).

Sample strain is calculated by $\Delta L/L_0$. $\Delta L$ is any additional extension between the grips after $L_0$ is reached and is recorded along with load at a rate of 50 Hz. Sample strain is expressed numerically (not as a percentage), thus a strain of 100% is 1.0 for the purposes of these calculations.

Record the sample strains at sample stresses of 3 gf/mm and at 7 gf/mm.

Tensile Modulus is the linear slope between 3 gf/mm and 7 gf/mm, and is calculated as:

Tensile Modulus=[7 gf/mm−3 gf/mm]/[sample strain at 7 gf/mm−sample strain at 3 gf/mm]

Repeat for 10 samples.

Elongation

The Elongation is measured during the Tensile Modulus test. The Elongation is the sample strain at a sample stress of 7 gf/mm. Elongation is expressed as a percent strain, e.g., a value of 1.0 strain from the Tensile Modulus method is expressed as 100% strain for Elongation.

Repeat and record the results for 10 samples. Calculate and record the average of the results. The average will be the Elongation value for the subject panty design.

Poisson Contraction Effect

The Poisson Contraction Effect is measured by stretching the sample in the direction of the longer dimension of the sample using a constant rate of extension tensile testing machine with computer interface, e.g., Instron; MTS; Zwick; etc., using a load cell for which the loads measured are within 10% to 90% of the limit of the cell, and ensures accuracy of a 5N load to 0.1N. The instrument is equipped with a single line contact grips, wider than 3 cm (ensures wider than the short axis of the sample). Prior to testing, calibrate the equipment according to the instruments manufacturer's recommendations.

The grips of the tensile testing machine consist of air actuated grips designed to hold the sample. No slippage should be permitted between the sample and the grips. The distance between the lines of gripping force (distance from one grip to the next, along the axis of the machine's elongation) should be 3 cm as measured by a steel rule held beside the grips. This distance will be referred to from here on as the "starting gauge-length".

The sample is mounted in the grips with its long axis parallel to the direction of applied elongation, and the center line of the long axis of the sample centered in each grip. 1 cm of each end of the sample's long axis is inserted into each grip, leaving 4 cm of the long axis of the sample between the grips. The starting gauge-length of 3 cm ensures some slack in the sample at the start of the test.

After the sample is mounted, the machine's load channel is set to zero (this eliminates the weight of the sample in the calculations). The grips are slowly moved apart at 5.08 cm/min (2.0 in/min) until a load of 5 gf (grams-force). The separation between the grips at this position is recorded as $L_0$.

($L_0$=starting gauge-length+additional machine extension to reach 5 gf).

After the 5 gf load is attained, extend the sample at a rate of 50.8 cm/min (20 in/min) with a data acquisition rate of 50 Hz. Extend until a stress of 7 gf/mm is reached. The machine's extension is stopped at the point, and the sample is held at this stress and accompanying strain.

For stress calculation, the thickness of the material is neglected, hence the stress values are recorded in units of gf/mm. Stress is calculated by dividing the load in the sample, as recorded by the load cell, by the sample width (short axis).

Sample strain is calculated by $\Delta L/L_0$. $\Delta L$ is any additional extension between the grips after $L_0$ is reached and is continuously recorded along with load at a rate of 50 Hz.

The narrowest width of the sample perpendicular to its long axis is measured to the nearest 0.5 mm using a steel rule ($W_n$). The narrowest width is typically at the center of the sample along its longer dimension.

The Poisson Contraction Effect (PCE) is calculated by:

$$PCE=[(W_0-W_n)/W_0]/[\Delta L/L_0]$$

Where:
$W_0$=sample lateral dimension prior to stretching
$W_n$=the narrowest dimension of the sample perpendicular to the stretch direction after stretching to a stress of 7 gf/mm
$L_0$=starting gauge-length+additional machine extension to reach 5 gf
$\Delta L$=additional extension between the grips after $L_0$ is reached at a sample stress of 7 gf/mm Repeat and record the results for 10 samples. Calculate and record the average of the results. The average will be the Poisson Contraction Effect value for the subject panty design.

Ordinary X-Y Plane Dimensions

For purposes herein, when a length or width of a feature of a panty is specified, it is to be measured with the panty laid out flat on a horizontal planar surface (in an opened or assembled configuration, as appropriate) with the material of the panty smoothed out flat, but in a relaxed condition, not pulled or stretched along any planar direction.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

In view of the foregoing disclosure, the following non-limiting examples are contemplated:

1. A durable underwear brief panty adapted to accommodate an absorbent component, comprising:
    a front waist portion (100) with a front waist edge (102) and left and right front leg opening edges (104);
    a rear waist portion (120) with a rear waist edge (122) and left and right rear leg opening edges (124);
    a crotch portion (130) with a forward portion (132) meeting the front waist portion, a rearward portion (136) meeting the rear waist portion, and left and right crotch leg opening edges (140), and a minimum width (CW) of 8.0 cm, more preferably 9.5 cm, and still more preferably 11.0 cm; and
    left and right hip side portions (160) joining the front waist portion to the rear waist portion and thereby forming a waist opening with a waist opening edge comprising the front waist edge (102) and the rear waist edge (122), and left and right leg openings each comprising a respective left or right front leg opening edge, crotch leg opening edge and rear leg opening edge;
    wherein, when the panty is in an opened configuration in which the front waist portion and rear waist portion are separated at the hip side portions, the panty has a longitudinal axis (200) and a lateral axis (300), with an intersection (250) thereof, the intersection occurring in the crotch portion (130); and
    wherein the crotch portion exhibits:
        a crotch longitudinal Elongation of 5 percent to 100 percent and a crotch longitudinal Tensile Modulus of 20 gf/mm to 100 gf/mm; and
        a crotch lateral Elongation of 50 percent to 200 percent and a crotch lateral Tensile Modulus of 2 gf/mm to 20 gf/mm.
2. The brief panty of example 1 wherein each of the front waist portion (100), rear waist portion (120) and crotch portion (130) comprises a knit material.
3. The brief panty of either of examples 1 or 2 wherein the crotch portion exhibits a Poisson Contraction Effect upon lateral stretching of 0.40 or less.
4. The brief panty of example 3 wherein the crotch portion exhibits a Poisson Contraction Effect upon lateral stretching of 0.1 to 0.40.
5. The brief panty of any of the preceding examples wherein the crotch portion exhibits a ratio of lateral Elongation to longitudinal Elongation of 3:1 to 40:1.
6. The brief panty of any of the preceding examples wherein the crotch portion exhibits a ratio of longitudinal Tensile Modulus to lateral Tensile Modulus of 3:1 to 50:1.
7. The brief panty of any of the preceding examples wherein the crotch portion comprises a section of rib knit fabric wherein the ribs are substantially aligned in a longitudinal direction.
8. The brief panty of any of the preceding examples wherein the knit material of any one or more of the front waist portion (100), rear waist portion (120) and crotch portion (130) comprises a combination of elastic and non-elastic fibers, threads or yarns.
9. The brief panty of any of the preceding examples, wherein:
    each of the front and rear waist portions exhibits a waist longitudinal Elongation of 5 percent to 100 percent and a waist longitudinal Tensile Modulus of 20 gf/mm to 100 gf/mm; and
    each of the front and rear waist portions exhibits a waist lateral Elongation of 50 percent to 200 percent and a waist lateral Tensile Modulus of 2 gf/mm to 20 gf/mm.
10. The brief panty of any of the preceding examples, wherein the crotch portion (130) comprises at least distinct wearer-facing and outward-facing layers (130*a*, 130*b*) of knit material at the intersection (250) between the longitudinal and lateral axes.
11. The brief panty of example 10 having a layer of absorbent material disposed between the wearer-facing and outward-facing layers of knit material, the absorbent material comprising a material selected from the group consisting of fibers or filaments of cotton, other natural plant-based fibers, rayon, polyester, polyamide or any combination thereof, the at least two layers of knit material being joined together about the absorbent material, to form an envelope structure containing the layer of absorbent material.
12. The brief panty of example 11 wherein the layer of absorbent material has a forward end, a rearward end and longitudinal side edges, and the layer of absorbent material is contained by the wearer-facing and outward-facing layers of knit material but is either (a) entirely unattached to the wearer-facing and outward-facing layers of knit material; (b) is not attached to the outward-facing layer of knit material; or (c) is not attached to the outward-facing layer of knit material at any opposing locations along the longitudinal side edges of the layer of absorbent material.
13. The brief panty of example 12 wherein the layer of absorbent material is attached one, but not both, of outward-facing layer (130*b*) and wearer-facing layer (130*a*) at a location along or proximate the longitudinal axis (200).
14. The brief panty of either of either of examples 10 or 11 wherein the at least two layers of knit material define an open envelope structure in the form of a pocket having an insertion/withdrawal opening and a pad containment space at least partially present in the crotch portion, between the at least two layers of knit material.
15. A combination of a brief panty of example 14 and a removable absorbent pad disposed in the open envelope structure.
16. A combination of a brief panty of any of examples 1-14, and an absorbent pad disposed adjacent a wearer-facing surface of the crotch portion.
17. The combination of example 16 wherein the absorbent pad is formed separately of the brief panty and comprises a liquid permeable topsheet, a liquid impermeable backsheet, and an absorbent core structure disposed between the topsheet and the backsheet; and a deposit of adhesive disposed between an outward-facing surface of the backsheet and the wearer-facing surface of the crotch portion.
18. An array of first and second products for managing incontinence, comprising the brief panty of any of examples 1-14 as the first product, and a separately provided absorbent pad as the second product.
19. The array of example 18 wherein the absorbent pad comprises a liquid permeable topsheet, a liquid impermeable backsheet and an absorbent core disposed between the topsheet and the backsheet.

20. The array of either of examples 17 or 18 wherein the absorbent pad comprises a deposit of adhesive on an outward-facing surface of the backsheet.

What is claimed is:

1. A durable underwear brief panty adapted to accommodate an absorbent component, comprising:
a front waist portion with a front waist edge and left and right front leg opening edges;
a rear waist portion with a rear waist edge and left and right rear leg opening edges;
a crotch portion with a forward portion meeting the front waist portion, a rearward portion meeting the rear waist portion, and left and right crotch leg opening edges, and a minimum width of 8.0 cm; and
left and right hip side portions joining the front waist portion to the rear waist portion and thereby forming a waist opening with a waist opening edge comprising the front waist edge and the rear waist edge, and left and right leg openings each comprising a respective left or right front leg opening edge, crotch leg opening edge and rear leg opening edge;
wherein, when the panty is in an opened configuration in which the front waist portion and rear waist portion are separated at the hip side portions, the panty has a longitudinal axis and a lateral axis, with an intersection thereof, the intersection occurring in the crotch portion; and
wherein the crotch portion exhibits:
a crotch longitudinal Elongation of 5 percent to 100 percent and a crotch longitudinal Tensile Modulus of 20 gf/mm to 100 gf/mm;
a crotch lateral Elongation of 50 percent to 200 percent and a crotch lateral Tensile Modulus of 2 gf/mm to 20 gf/mm; and
a Poisson Contraction Effect upon lateral stretching of 0.40 or less.

2. The brief panty of claim 1 wherein each of the front waist portion, rear waist portion and crotch portion comprises a knit material.

3. The brief panty of claim 2 wherein the knit material comprises a combination of elastic and non-elastic fibers, threads or yarns.

4. The brief panty of claim 1 wherein the crotch portion exhibits a Poisson Contraction Effect upon lateral stretching of 0.1 to 0.40.

5. The brief panty of claim 1 wherein the crotch portion exhibits a ratio of lateral Elongation to longitudinal Elongation of 3:1 to 40:1.

6. The brief panty of claim 1 wherein the crotch portion exhibits a ratio of longitudinal Tensile Modulus to lateral Tensile Modulus of 3:1 to 50:1.

7. The brief panty of claim 1 wherein the crotch portion comprises a section of rib knit fabric wherein the ribs are substantially aligned in a longitudinal direction.

8. The brief panty of claim 1, wherein:
each of the front and rear waist portions exhibits a waist longitudinal Elongation of 5 percent to 100 percent and a waist longitudinal Tensile Modulus of 20 gf/mm to 100 gf/mm; and
each of the front and rear waist portions exhibits a waist lateral Elongation of 50 percent to 200 percent and a waist lateral Tensile Modulus of 2 gf/mm to 20 gf/mm.

9. The brief panty of claim 1, wherein the crotch portion comprises at least distinct wearer-facing and outward-facing layers of knit material at the intersection between the longitudinal and lateral axes.

10. The brief panty of claim 9 having a layer of absorbent material disposed between the wearer-facing and outward-facing layers of knit material, the absorbent material comprising a material selected from the group consisting of fibers or filaments of cotton, other natural plant-based fibers, rayon, polyester, polyamide or any combination thereof, the at least two layers of knit material being joined together about the absorbent material, to form an envelope structure containing the layer of absorbent material.

11. The brief panty of claim 10 wherein the layer of absorbent material has a forward end, a rearward end and longitudinal side edges, and the layer of absorbent material is contained by the wearer-facing and outward-facing layers of knit material but is either (a) entirely unattached to the wearer-facing and outward-facing layers of knit material; (b) is not attached to the outward-facing layer of knit material; or (c) is not attached to the outward-facing layer of knit material at any opposing locations along the longitudinal side edges of the layer of absorbent material.

12. The brief panty of claim 11 wherein the layer of absorbent material is attached to one, but not both, of outward-facing layer and wearer-facing layer at a location along or proximate the longitudinal axis.

13. The brief panty of claim 9 wherein the at least two layers of knit material define an open envelope structure in the form of a pocket having an insertion/withdrawal opening and a pad containment space at least partially present in the crotch portion, between the at least two layers of knit material.

14. A combination of a brief panty of claim 13 and a removable absorbent pad disposed in the open envelope structure.

15. A combination of a brief panty of claim 1, and an absorbent pad disposed adjacent a wearer-facing surface of the crotch portion.

16. The combination of claim 15 wherein the absorbent pad is formed separately of the brief panty and comprises a liquid permeable topsheet, a liquid impermeable backsheet, and an absorbent core structure disposed between the topsheet and the backsheet; and a deposit of adhesive disposed between an outward-facing surface of the backsheet and the wearer-facing surface of the crotch portion.

17. An array of first and second products for managing incontinence, comprising the brief panty of claim 1 as the first product, and a separately provided absorbent pad as the second product.

18. The array of claim 17 wherein the absorbent pad comprises a liquid permeable topsheet, a liquid impermeable backsheet and an absorbent core disposed between the topsheet and the backsheet.

19. The array of claim 18 wherein the absorbent pad comprises a deposit of adhesive on an outward-facing surface of the backsheet.

* * * * *